(12) United States Patent
Lundahl et al.

(10) Patent No.: US 8,609,073 B2
(45) Date of Patent: Dec. 17, 2013

(54) COMPOSITIONS AND METHODS FOR REDUCING PHOTOSENSITIVITY ASSOCIATED WITH PHOTODYNAMIC THERAPY

(75) Inventors: Scott Lundahl, Lexington, MA (US); Stuart Marcus, Mount Kisco, NY (US)

(73) Assignee: Dusa Pharmaceuticals, Inc., Wilmington, MA (US)

( * ) Notice: Subject to any disclaimer, the term of this patent is extended or adjusted under 35 U.S.C. 154(b) by 1233 days.

(21) Appl. No.: 11/817,455

(22) PCT Filed: Mar. 3, 2006

(86) PCT No.: PCT/US2006/007558
§ 371 (c)(1),
(2), (4) Date: Aug. 15, 2008

(87) PCT Pub. No.: WO2006/096492
PCT Pub. Date: Sep. 14, 2006

(65) Prior Publication Data
US 2009/0123400 A1    May 14, 2009

Related U.S. Application Data

(60) Provisional application No. 60/658,367, filed on Mar. 4, 2005.

(51) Int. Cl.
*A61K 8/00* (2006.01)
*A61Q 17/04* (2006.01)

(52) U.S. Cl.
USPC ............ 424/60; 424/9.3; 424/9.362; 424/9.6; 424/59

(58) Field of Classification Search
USPC .......... 424/9.3, 9.362, 59, 9.6, 9.61; 514/183, 514/184, 185, 186, 312, 410, 554; 606/4
See application file for complete search history.

(56) References Cited

U.S. PATENT DOCUMENTS

| 5,079,262 | A |   | 1/1992 | Kennedy et al. |
|---|---|---|---|---|
| 5,211,938 | A |   | 5/1993 | Kennedy et al. |
| 5,234,940 | A |   | 8/1993 | Kennedy et al. |
| 5,422,093 | A |   | 6/1995 | Kennedy et al. |
| 5,556,612 | A | * | 9/1996 | Anderson et al. ............... 424/59 |
| 5,955,490 | A |   | 9/1999 | Kennedy et al. |
| 6,114,321 | A | * | 9/2000 | Platzek et al. ................ 514/185 |
| 6,476,014 | B1 | * | 11/2002 | Jordan et al. ................. 514/187 |
| 6,492,420 | B2 |   | 12/2002 | Gierskcky et al. |
| 6,683,175 | B2 |   | 1/2004 | Tanaka |
| 6,693,093 | B2 |   | 2/2004 | Chowdhary et al. |
| 6,710,066 | B2 | * | 3/2004 | Kennedy et al. .............. 514/410 |
| 6,750,212 | B2 |   | 6/2004 | Peng et al. |
| 6,753,160 | B2 |   | 6/2004 | Adair |
| 2003/0083649 | A1 | * | 5/2003 | Margaron et al. ................. 606/4 |
| 2004/0259855 | A1 | * | 12/2004 | Anderson et al. ............. 514/185 |

OTHER PUBLICATIONS

Fubao Lin et al., Protoporphyrin IX-Sensitized Photoinactivation of 5-aminolevulinate Treated Leukemia Cells: Effects of Exogenous Iron, Photochemistry and Photobiology, 1999, 69(3) 375-381.*
Bech et al., "A Hydroxypyridinone (CP94) Enhances Protoporphyrin IX Formation on 5-Aminolaevulinic Acid Treated Cell," Journal of Photochemistry and Photobiology B: Biology, 1997, 41:136-44.
Bhasin et al., "Protoporphyrin-IX Accumulation and Cutaneous Tumor Regression in Mice Using a Ferrochelatase Inhibitor," Cancer Letters, 2002, 187(1-2):9-16.
Labbe et al., "Zinc protoporphyrin: A metabolite with a mission," Clinical Chemistry, 1999, 45(12):2060-72.
Lin et al., "Protoporphyrin IX-Sensitized Photoinactivation of 5-Aminolevulinate-Treated Leukemia Cells: Effects of Exogenous Iron," Photochemistry and Photobiology, 1999, 69(3):375-81.
Lin et al., "Stimulatory and Inhibitory Effects of Iron on Photodynamic Inactivation of Leukemia Cells," Photochemistry and Photobiology, 1995, 62(3):528-34.
Tan et al., "Enhancement of Photodynamic Therapy in Gastric Cancer Cells by Removal of Iron," GUT, 1997, 41:14-18.

* cited by examiner

*Primary Examiner* — Michael G Hartley
*Assistant Examiner* — Jagadishwar Samala
(74) *Attorney, Agent, or Firm* — Foley & Lardner LLP

(57) ABSTRACT

The present invention provides compositions and methods for decreasing photosensitivity induced by photodynamic therapy (PDT). The compositions and methods of the present method employ porphyrin complexing molecules as agents for reducing photosensitivity.

20 Claims, 5 Drawing Sheets

COMPOSITIONS AND METHODS FOR REDUCING PHOTOSENSITIVITY ASSOCIATED WITH PHOTODYNAMIC THERAPY

FIELD OF THE INVENTION

This invention relates generally to use of and agents for reducing the side effects associated with photodynamic therapy.

BACKGROUND OF THE INVENTION

Photochemotherapy and photodynamic therapy (PDT) are two techniques used to detect and/or treat tissue abnormalities. These techniques are based on the discovery made over 90 years ago that unicellular organisms, i.e., certain rapidly growing cells (such as cells of the Lower Kingdom, now referred to as Protista), treated with certain chemicals will die when exposed to light. Thus, synthetic porphyrins have been shown in vitro to protect cells from infections caused by organisms such as parasites, e.g., tyromastigotes and sphaeromastigotes of *Tyropanosoma cruzi*, J. PARASITOL., 75(6) 1989, p. 970-976, and gram positive bacteria, mycoplasma and yeasts, Malik et al. J. PHOTOCHEMISTRY AND PHOTOBIOLOGY, B. BIOLOGY 5 281-293 (1990). *P. acne* is known to, in vitro, produce intracellular protoporphyrin in the presence of exogenous ALA. Kjeldstad, Conference on Photosensitization and Photochemotherapy of Cancer, Det Norske Videnskaps-Akademi, Mar. 16-17, 1993, Oslo, Norway.

PDT has been approved for the palliation of malignant dysphagia, treatment of early recurrent lung cancer, palliation of endobronchial destruction, treatment of wet AMD, and treatment of nonhypertrophic facial actinic keratoses. The patient is given a photo-activatable drug that has some degree of specificity for the tissue being treated. A tissue volume that includes the target tissue is then exposed to photoactivating light so as to destroy the target tissue while causing only mild and reversible damage to the other tissues in the same treatment volume. A more detailed description of the uses of PDT are described in Marcus et al., EXPERT OPINION ON EMERGING DRUGS, 7(2):321-34 (2002), which is hereby incorporated by reference in its entirety.

One class of photodynamic therapy agents currently being used are porphyrins and related photosensitizers. These agents are given systemically (by intravenous injection), although occasionally they are given either topically or by intralesional injection. They can be activated by visible (red) light. The localized exposure of porphyrin-containing tissues to such light ordinarily does not induce a chemical reaction between cell components and the porphyrin molecules. Instead, the porphyrins act as catalysts by trapping the energy of the photoactivating light and then passing it on to molecules of oxygen, which in turn are raised to an excited state that is capable of oxidizing adjacent molecules or structures. Cell death is not caused primarily by damage to the DNA, but by damage to essential membrane structures. The goal of photodynamic therapy is sometimes cure (mainly for carcinomas), but usually the goal is palliation through local control when none of the standard forms of therapy are considered likely to offer a significant degree of benefit to the patient.

Another class of agents, aside from porphyrins, relates to agents which can be administered either systemically or topically and which are not themselves photosensitizers, but which induce the synthesis of protoporphyrin IX (PpIX). One such agent is 5-Amino-4-oxopentanoic acid, also known as 5-aminolevulinic acid or δ-aminolevulinic acid ("ALA"), has been described for detecting and treating rapidly growing cells. In addition to the use ALA, prodrugs of 5-aminolevulinic acid, such as esters of 5-aminolevulinic acid could be administered to a patient to induce the synthesis of PpIX. For example, U.S. Pat. Nos. 6,710,066 by Kennedy et al., 5,079,262 by Kennedy et al., 5,211,938 by Kennedy et al., 5,234,940 by Kennedy et al., 5,422,093 by Kennedy et al., 5,955,490 by Kennedy et al., 6,750,212 by Peng et al., and 6,492,420 by Gierskcky et al., each of which is hereby incorporated by reference in its entirety, teach the use of ALA. ALA has also been reported for use in attenuating the growth and killing of plants and insects when applied directly to such organisms followed by exposure to light, based on work of Rebeiz et al. In vivo, ALA leads to increased production of protoporphyrin IX, which is a porphyrin that induces photosensitivity.

Synthetic porphyrins have also been used as photodynamic therapeutic agents in treating rapidly growing, e.g. rapidly dividing or rapidly metabolizing infectious cells, such as infectious pathogens, including protozoal parasites, such as *Plasmodium falciparum* (which causes malaria in humans), various other species of *Plasmodia, Leishmania*, and amoebae, pathogenic fungi, and microplasma, including the various parasitic forms, all such cells and organisms being referred to herein as Protista. The term Protista as used here and in the literature refers to the lowest orders of the animal and vegetable kingdoms, single celled or collections of single celled organisms including: the eukaryotes, including protozoa, fungi and algae, and the prokaryotes, which are bacteria and blue-green algae.

At present, the most commonly used porphyrins for photodynamic therapy are Hematoporphyrin IX (HpIX), Hematoporphyrin derivative (HpD), and various semi-purified preparations of HpD such as commercially available Photofrin® II, a semi-purified form of HpD. When porphyrins are used as photosensitizers, cell death results from damage to cell membranes. Consequently, malignant transformation is not a serious problem.

However, the use of photosensitizers in photodynamic therapy does suffer from a major problem. Photosensitizing concentrations persist in the skin for several weeks to several months following their administration. Consequently, severe accidental phototoxic skin reactions may occur unless the patient avoids exposure to sunlight (either direct, or filtered through window glass) until the concentration of the photosensitizer in the skin has been reduced to a harmless level. At present, the problem of photosensitivity following the administration of the photosensitizer is handled by advising the patient to avoid any form of exposure to sunlight (or to very bright artificial lights) for a period of at least two weeks post-injection, and to initiate subsequent exposure to sunlight very cautiously. Not all patients comply with these instructions, since it often is quite inconvenient to do so. In addition, the use of a sunscreen with a high blocking factor is recommended with warning that this will only reduce the hazard somewhat, not eliminate it completely. In a few cases, patients whose photosensitization persisted for more than a month post-treatment have been given large daily doses of beta-carotene over a period of several months in an attempt to prevent accidental phototoxic damage. Finally, attempts have been made to reduce phototoxicity by applying the photosensitizer topically to a limited area. However, the success at reducing phototoxicity has been limited, and there is a need for compositions and methods that may be used to reduce photosensitivity in patients undergoing photochemotherapy.

SUMMARY OF THE INVENTION

One embodiment of the invention provides a pharmaceutical composition comprising a porphyrin complexing molecule in an amount sufficient to reduce photosensitivity compared to the photosensitivity in a person who has not been treated with said pharmaceutical composition.

Another embodiment of the invention provides a photodynamic therapy kit comprising a first pharmaceutical composition comprising an agent which is not a photosensitizer but induces the synthesis or accumulation of protoporphyrin IX and a second pharmaceutical composition comprising a porphyrin complexing molecule for sequential or simultaneous administration to a patient.

Yet another embodiment of the invention provides a method of reducing post-photodynamic treatment photosensitivity in a patient comprising administering an effective amount of a porphyrin complexing molecule to the patient.

Still another embodiment of the invention provides a method for treating or detecting in a human patient a skin lesion that preferentially accumulates a photoactivatable porphyrin, comprising (A) administering to said human patient in need thereof an effective amount of a precursor of protoporphyrin IX and a porphyrin complexing molecule and (B) exposing the skin lesion to light capable of photoactivating protoporphyrin IX.

Other embodiments of the present invention and variations on these specific embodiments can be readily determined by one of ordinary skill in the art and are contemplated as part of the present invention.

DETAILED DESCRIPTION

Figure 1:
FIG. 1 shows the forearm of a test subject shortly after application of an ALA mixture according to example 1.

The present invention provides compositions and methods for decreasing photosensitivity induced by photodynamic therapy. The compositions and methods employ a porphyrin complexing molecule to decrease photosensitivity in a patient undergoing photodynamic therapy. In one embodiment, iron or an iron donating compound is incorporated into PpIX to decrease photosensitivity. These compositions and methods can be used to reduce the photosensitivity in patients undergoing photodynamic therapy thereby reducing the incidence of phototoxic reactions that have previously been a major drawback to photodynamic therapy. The compositions and methods may be used to reduce the duration of photosensitivity and/or reduce the severity of photosensitivity.

The following detailed description of the invention illustrates certain exemplary embodiments and allows a better understanding of the claimed invention.

Unless otherwise specified, "a", "an", and "the" mean "one or more."

A "porphyrin complexing molecule" is a molecule that can form a complex with a photosensitizing porphyrin to directly reduce or eliminate the photosensitizing effects of the porphyrin or facilitate a biochemical reaction wherein the porphyrin is converted to a non-photosensitizing form. For example, iron in the presence of PpIX is a porphyrin complexing molecule, because iron is incorporated into PpIX, the chelator, in the presence of ferrochelatase to form heme. Generally, metals are exemplary porphyrin complexing molecules. The "porphyrin complexing molecule" can be in atomic form and/or a portion of a larger molecule.

The basic structure of porphyrins consists of four pyrrole units linked by four methine bridges as shown in the figure below.

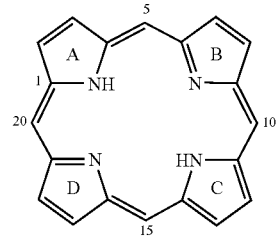

This basic structure can be modified in a number of ways to obtain different porphyrin structures. For example, derivatized porphyrins may be obtained using electrophilic substitution reactions typically used with aromatic compounds, such as porphyrins. Not all porphyrins are photosensitizers, but a number of porphyrin photosensitizers are known, including, but not limited to, protoporphyrin IX, Hematoporphyrin IX (HpIX), Hematoporphyrin derivative (HpD), benzoporphyrin derivative (BPD verteporfin), and various semi-purified preparations of HpD such as commercially available Photofrin® II.

An important feature of porphyrins is their ability to be metalated and demetalated. A number of metals, such as Fe, Zn, Cu, and Ni, can be inserted into the porphyrin cavity by using various metal salts. For example, iron is incorporated into PpIx in vivo in the presence of ferrochelatase to form heme, as discussed in detail below. Removal of the metal (demetalation) can usually be achieved by treatment with acids of various strengths.

Protoporphyrin IX is a common protoporphyrin manipulated for use in photodynamic therapy. PpIX, a naturally occurring photosensitizer, is the immediate precursor of heme in the heme biosynthetic pathway. All nucleated cells have at least a minimal capacity to synthesize PpIX, since heme is necessary for the synthesis of various essential heme-containing enzymes. Certain types of cells and tissues can synthesize relatively large quantities of PpIX. Under normal conditions, the synthesis of PpIX in such tissues is under such tight feed-back control that the cells produce it at a rate just sufficient to match their need for heme. However, the usual rate-limiting step in the process, the synthesis of 5-aminolevulinic acid (ALA), can be bypassed by the provision of exogenous ALA, porphobilinogen, or other precursor of PpIX. Certain tissues and organs will then accumulate such a large excess of PpIX that they become both fluorescent and photosensitive. At least in the case of the skin, the PpIX appears to be synthesized in situ. ALA, which is commercially available from Sigma Chemical Company and other sources and which is water soluble, can be administered orally, topically or by injection. The oral and parenteral routes lead to the induction of clinically useful concentrations of PpIX in certain benign and malignant tissues throughout the body. PpIX is converted into heme by the incorporation of iron into PpIX in the presence of ferrochelatase. In this manner, PpIX is converted to a material that is not a photosensitizer. This biochemical pathway has been investigated. For example, Lin et al., *Protoporphyrin IX-Sensitized Photoinactivation of 5-Aminolevulinate-Treated Leukemia Cells: Effects of Exogenous Iron*, PHOTOCHEMISTRY AND PHOTOBIOLOGY, 69(3):375-81 (1999); Bech et al., *A Hydroxypyridinone (CP94) Enhances Protoporphyrin IX Formation On 5-Aminolaevulinic Acid Treated Cell*, JOURNAL OF PHOTOCHEMISTRY AND PHOTOBIOLOGY B: BIOLOGY 41:136-44 (1997); Tan et al., *Enhancement Of Photodynamic Therapy In Gastric Cancer Cells By Removal Of Iron*, GUT 41:14-18 (1997); Lin et al., *Stimulatory And Inhibitory Effects Of Iron On Photodynamic Inactivation Of Leukemia Cells*, PHOTOCHEMISTRY AND PHOTOBIOLOGY, 62(3):528-34 (1995); Bhasin et al., *Protoporphyrin-IX Accumulation And Cutaneous Tumor Regression In Mice Using A Ferrochelatase Inhibitor*, CANCER LETTERS 187(1-2): 9-16 (2002), each of which is hereby incorporated by reference in its entirety, all investigate the conversion of PpIX to heme in the presence of iron and ferrochelatase.

The present invention provides compositions comprising a porphyrin complexing molecule to reduce photosensitivity in patients and methods of using these compositions. This reduction in photosensitivity overcomes the major limitation of photodynamic therapy, which is prolonged photosensitivity after photodynamic treatment.

1. Porphyrin Complexing Molecule Compositions

The present inventions provide compositions comprising a porphyrin complexing molecule. The porphyrin can be any photosensitizing porphyrin, such as PpIX. Any suitable porphyrin complexing molecule can be used, such as a molecule that is chelated by the porphyrin. Examples of suitable molecules include, but are not limited to, silver (Ag), aluminum (Al), cadmium (Cd), cobalt (Co), chromium (Cr), copper (Cu), iron (Fe), gadolinium (Gd), indium (In), lutetium (Lu), magnesium (Mg), manganese (Mn), nickel (Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn). Generally, metals, such as $Fe^{++}$ and $Zn^{++}$, are examples of molecules than can be incorporated into photosensitizing porphyrins to reduce photosensitivity. The incorporation of $Fe^{++}$ into PpIX produces heme, and $Zn^{++}$ can be incorporated into PpIX to form zinc protoporphyrin (ZnPP) as discussed in Labbe et al., *Zinc protoporphyrin: A metabolite with a mission*, CLINICAL CHEMISTRY 45(12):2060-72 (1999), which is hereby incorporated by reference.

The porphyrin complexing molecule can be delivered alone or as part of another molecule or complex. For example, iron can be free iron or the iron can be part of an iron donating compound, such as ferric-8-hydroxyquinoline ($Fe[HQ]_2$) or $FeCl_2$. The porphyrin complexing molecule can be covalently bound to the other molecule, or it may be bound in some other way, such as by intermolecular forces. The porphyrin complexing molecule can be combined with another molecule for ease of administration. For example, a metallic ion may be administered as part of a complex that can readily pass through cell membranes. The molecule that is incorporated into the photosensitizing porphyrin may also be attached to another molecule that can be used for detection. For example, the porphyrin complexing molecule can be attached to a magnetic molecule, a fluorescent molecule, or a radioactive molecule. In some embodiments, the porphyrin complexing molecule itself can be functionalized to allow detection. For example, the porphyrin complexing molecule can be radioactive. This can allow the detection and quantification (e.g. concentration, location, etc.) of the molecule delivered.

In some embodiments, the compositions comprise more than one type of porphyrin complexing molecule. For example, the composition can comprise two different metals, such as zinc and iron. These metals can be in ionic or atomic form or part of the same or different compounds. For example, the composition can comprise iron provided as ferric-8-hydroxyquinoline and also contain atomic zinc. The composition can also comprise the same type of porphyrin complexing molecule in two or more forms. For example, the composition can comprise iron delivered as both ferric-8-hydroxyquinoline and atomic iron. By varying the types and/or forms of the porphyrin complexing molecules, compositions can be formed that have varying characteristics. If one molecule is more rapidly incorporated than another type, the ratio of the two molecules can be adjusted to control the rate of reduction in photosensitivity.

The compositions of the present invention may comprise one or more additional compounds. For example, the compositions of the present invention can comprise a sunscreen. Any suitable sunscreen can be used including sunscreens that block damaging light and sunscreens that absorb damaging light. The sunscreen can be selected from the group consisting of aminobenzoic acid, padimate O, oxybenzone, titanium dioxide, avobenzone, octocrylene, octyl salicylate, octyl methoxycinnamate, dioxybenzone, oxybenzone, homosalate, octyl methoxycinnamate, menthyl anthranilate, lisadimate phenylbenzimidazole, sulisobenzone, and trolamine salicylate. The sunscreen can be incorporated so that when the composition is administered, the sunscreen immediately reduces photosensitivity until the porphyrin complexing molecule can act sufficiently to reduce photosensitivity. The sunscreen can also be used to simply provide further protection against phototoxic reactions.

The compositions of the present invention can comprise a precursor of a photosensitive porphyrin. Examples of suitable precursors include, but are not limited to, ALA and porphobilinogen. U.S. Pat. Nos. 6,710,066 by Kennedy et al., 6,750,212 by Peng et al., and 6,492,420 by Gierskcky et al., each of which is hereby incorporated by reference in its entirety, teach different precursors and methods of formulating and administering the precursors. A composition comprising both a precursor of a photosensitive phorphyrin along with a porphyrin complexing molecule can be used as a photodynamic therapy composition. Such a photodynamic therapy composition may be used to reduce the risk of phototoxic reactions occurring after the completion of photodynamic therapy. In some embodiments, the composition can be formulated, so the precursor induces sufficient photosensitivity for photodynamic therapy while the porphyrin complexing molecule reduces the photosensitivity after the therapy.

Porphyrin complexing molecule compositions can be in forms suitable for oral, injection (intravenous, subcutaneous, intramuscular, intraperitoneal, or intramammary), intranasal, intratracheal, or topical administration. Oral compositions may be in aqueous or oil solution, suspension, tablet, capsule, or pill form, for example. Compositions for topical administration may be formed for administration to skin and/or mucosal membranes. Compositions for injection may be in any form suitable for administration, such as an aqueous suspension or an emulsion. Compositions for inhalation may be in any form suitable for administration, such as a suspension, mist, or powder. Compositions for topical administration may be in forms, such as, but not limited to, gels, creams, lotions, suspensions, emulsions, ointments, foams, pastes, or powders.

Topical formulations are a preferred form of the compositions comprising at least one porphyrin complexing molecule. The topical compositions can be applied at least once daily. In some embodiments, the compositions can be applied at least twice daily, and in other embodiments, the compositions can be employed at least three times daily. The compositions may comprise at least 2% by weight of the at least one porphyrin complexing molecule. In some embodiments, the composition comprising at least one porphyrin complexing molecule can contain at least 5% wt. of, at least 10% wt. of, at least 20% wt. of, at least 30% wt., or at least 50% wt. of the at least one porphyrin complexing molecule. The topical compositions can include a variety of ingredients, such as carriers, thickeners and/or gelling agents, fragrances, and coloring. Topical compositions can also include ingredients, such as emollients and moisturizers. These ingredients may be used to sooth the skin or repair damage caused by the photodynamic therapy.

Porphyrin complexing molecule compositions can be made into gel form by using gelling agents. Suitable gelling agents include, for example, hydrogels such as, Natrosol® 250H NF (Hercules, Inc. Wilmington, Del.). A hydrogel can be added at a concentration of about 0.5 wt % to about 5 wt %, based on the total volume of the gel. Other suitable gelling agents include, but are not limited to, about 0.05 wt % to about 3 wt % cellulose polymer, such as cellulose gum or cationic guar derivatives, and up to about 10 wt % petrolatum, glycerin, polyethylene glycol, incroquat behenyl TMS, cetyl palmitate, glycerol stearate, agarose and the like. These gel compositions can be applied alone or using an adhesive after photodynamic therapy. Gelling agents and/or thickeners can also be used to thicken the composition to form compositions in the form of pastes, ointments, and creams, for example.

Porphyrin complexing molecule compositions can comprise a pharmaceutically acceptable carrier. A pharmaceutically acceptable carrier or excipient suitable for a solid preparation, such as tablets or capsules, can be, for example, binders (e.g., acacia, gelatin, dextrin, hydroxypropylcellulose, methylcellulose, polyvinylpyrrolidone), solvents, dispersion media, diluents (e.g., lactose, sucrose, mannitol, corn starch, potato starch, calcium phosphate, calcium citrate, crystalline cellulose), lubricants (e.g., magnesium stearate, calcium stearate, stearic acid, talc, anhydrous silicic acid), disintegrants (e.g., corn starch, potato starch, carboxymethylcellulose, carboxymethylcellulose calcium, alginic acid), and wetting agents (e.g., sodium laurylsulfate). A pharmaceutically acceptable carrier or excipient suitable for a liquid preparation, such as solutions or suspensions, can be, for example, aqueous vehicles (e.g., water), suspending agents (e.g., acacia, gelatin, methyl cellulose, carboxymethylcellulose sodium, hydroxymethyl-cellulose, aluminum stearate gel), surfactants (e.g., lecithin, sorbitan monooleate, glycerin monostearate), and non-aqueous vehicles (e.g., glycerin, propylene glycol, vegetable oil). Moreover, compositions can contain preservatives, such as, p-hydroxybenzoic acid methyl ester, and p-hydroxybenzoic acid propyl ester.

Suitable carriers include, but are not limited to, calcium carbonate, carboxymethylcellulose, cellulose, citric acid, dextrate, dextrose, ethyl alcohol, glucose, hydroxymethylcellulose, lactose, magnesium stearate, maltodextrin, mannitol, microcrystalline cellulose, oleate, polyethylene glycols, potassium diphosphate, potassium phosphate, saccharose, sodium diphosphate, sodium phosphate, sorbitol, starch, stearic acid and its salts, sucrose, talc, vegetable oils, water, organic esters, and combinations comprising one or more of the foregoing carriers. Additional examples of pharmaceutical carriers for use in this invention include those described in REMINGTON'S PHARMACEUTICAL SCIENCES, 15th Ed. Easton: Mack Publishing Co. pp. 1405-1412 and 1461-1487 (1975), and THE NATIONAL FORMULARY XIV 14th Ed., Washington: American Pharmaceutical Association (1975), which references are hereby incorporated by reference in their entirety. The use of such media and agents for pharmaceutically active substances is well known in the art. One of ordinary skill in the art can readily select a suitable carrier or carriers.

Compositions of the present invention can further comprise an emollient, especially when the composition is intended for topical administration. Suitable emollients include, but are not limited to, glycerin, propylene glycol, and similar ingredients disclosed in the INTERNATIONAL COSMETIC INGREDIENT DICTIONARY AND HANDBOOK Vol. 4 (9th. ed. 2002), more particularly the emollients disclosed on pages 2930-2936. The disclosure of the INTERNATIONAL COSMETIC INGREDIENT DICTIONARY AND HANDBOOK Vol. 4, pages 2930-2936, is hereby incorporated by reference in its entirety.

Porphyrin complexing molecule compositions can be packaged as part of a kit. The kit can include both the porphyrin complexing molecule and a photodynamic therapy composition. The photodynamic therapy composition can be any compound that induces photosensitivity in a patient. For example, the photodynamic therapy composition can be a precursor of PpIX, such as ALA or a prodrug thereof. The porphyrin complexing molecule composition can be applied before, after, or simultaneously with the photosensitizer composition.

2. Methods of Reducing Photosensitivity

The present invention provides a method of reducing post-photodynamic treatment photosensitivity in a patient comprising administering an effective amount of a porphyrin complexing molecule to the patient. The present invention also provides a method for treating or detecting in a human patient a skin lesion that preferentially accumulates a photoactivatable porphyrin, comprising administering to said human patient in need thereof an effective amount of a precursor of protoporphyrin IX and a porphyrin complexing molecule and exposing the skin lesion to light capable of photoactivating protoporphyrin IX.

The porphyrin complexing molecule can be administered as a composition. Exemplary compositions comprising a porphyrin complexing molecule are those described herein. These methods reduce or eliminate the danger of post-photodynamic treatment phototoxicity that has previously been a drawback of photodynamic treatment.

The porphyrin complexing molecule can be any molecule that is either administered sequentially or simultaneously with the photosensitizing agent to reduce the photosensitizing effects. Examples of suitable molecules as recited above and include, but are not limited to, silver (Ag), aluminum (Al), cadmium (Cd), cobalt (Co), chromium (Cr), copper (Cu), iron (Fe), gadolinium (Gd), indium (In), lutetium (Lu), magnesium (Mg), manganese (Mn), nickel Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn). Generally, metals, such as $Fe^{++}$ and $Zn^{++}$, are molecules than can be incorporated into photosensitizing porphyrins to reduce photosensitivity. The incorporation of $Fe^{++}$ into PpIX in the presence of ferrochelatase produces heme, and $Zn^{++}$ can be incorporated into PpIX to form zinc protoporphyrin (ZnPP) as discussed in Labbe et al., *Zinc protoporphyrin: A metabolite with a mission*, CLINICAL CHEMISTRY 45(12):2060-72 (1999), which is hereby incorporated by reference.

The photodynamic therapy can be a therapy where a patient is administered a photosensitizing compound. Photosensitizing compounds include both photosensitizing porphyrins and precursors of photosensitizing porphyrins. Examples of photosensitizing porphyrins include, but are not limited to, protoporphyrin IX, Hematoporphyrin IX (HpIX), Hematoporphyrin derivative (HpD), benzoporphyrin derivative (BPD verteporfin), and various semi-purified preparations of HpD such as commercially available Photofrin® II. Examples of precursors of photosensitizing porphyrins include ALA and prodrugs thereof and porphobilinogen and those taught in U.S. Pat. Nos. 6,710,066 by Kennedy et al., 6,750,212 by Peng et al., and 6,492,420 by Giersckcly et al., each of which is hereby incorporated by reference in its entirety, by teach the use of ALA. In some embodiments, the photodynamic treatment can involve the administration of a PpIX precursor, such as ALA, and the porphyrin complexing molecule can be iron or an iron donating compound.

The porphyrin complexing molecule can be administered to the patient before, after, or during the photodynamic therapy. For example, the porphyrin complexing molecule can be administered before a photosensitizing composition is administered. It can also be administered at the same time as a separate composition or part of the photosensitizing composition. The porphyrin complexing molecule can also be applied after a photosensitizing composition and either before, after, or during exposure to the therapeutic light source. In some embodiments, the porphyrin complexing molecule may be applied at two or more different times. For example, the porphyrin complexing molecule can be applied simultaneously with a photosensitizing composition and also applied at least once afterwards to reduce photosensitivity.

An additional agent to reduce photosensitivity or otherwise reduce the risk of phototoxic reactions can also be administered with the porphyrin complexing molecule. Examples of such agents, include sunscreens, such as those described herein. These additional agents can be applied before, after, or simultaneously with the porphyrin complexing molecule. The additional agents can be administered as part of the same or a different composition from the porphyrin complexing molecule composition.

The porphyrin complexing molecule can be administered in compositions of any form. For example, forms suitable for oral, injection (intravenous, subcutaneous, intramuscular, intraperitoneal, or intramammary), intranasal, intratracheal, or topical administration can be administered. Oral compositions may be in aqueous solution, suspension, tablet, capsule, or pill form, for example. Compositions for topical administration may be formed for administration to skin and/or mucosal membranes. Compositions for injection may be in any form suitable for administration, such as an aqueous suspension or an emulsion. Compositions for inhalation may be in any form suitable for administration, such as a suspension, mist, or powder. Compositions for topical administration may be in forms, such as, but not limited to, gels, creams, lotions, suspensions, emulsions, ointments, foams, pastes, or powders.

Dosages can be readily determined by one of ordinary skill in the art based on the porphyrin complexing molecule used and the route of administration. The composition comprising the porphyrin complexing molecule can include at least 5%, at least 15%, or at least 30% by weight of the porphyrin complexing molecule. The porphyrin complexing molecule can be administered at least once daily, at least twice daily, or at least three time daily in some embodiments. In some embodiments, the porphyrin complexing molecule is administered only once. Topical compositions comprising a porphyrin complexing molecule are a preferred form of administration. These topical compositions can comprise at least 5% by weight of the porphyrin complexing molecule.

EXAMPLE 1

Figure 2:
FIG. 2 shows the forearm of the test subject shown in FIG. 1 under UV illumination after overnight incubation after application of the ALA mixture.

The left inside forearm of an anonymous male volunteer was chosen as a test area for a composition comprising about 5% ferric chloride. The test area was first tape stripped and washed with acetone to enhance the amount and the uniformity of ALA uptake. A 20% mixture of 5-aminolevulenic acid (ALA) in a Eucerin base was then applied on the left inside forearm and allowed to incubate overnight. FIG. 1 shows the test area shortly after the application of the ALA mixture. FIG. 2 shows the test area shortly after overnight incubation. The figure shows PpIX fluorescence under UV illumination. Note the bright, punctuate fluorescence extending along the tape stripped side indicating the photosensitizing effects of PpIX.

Figure 3:
FIG. 3 shows the forearm of the test subject of FIG. 1 with PpIx induced florescence under UV illumination immediately after application of test mixture.

A mixture of about 5% ferric chloride and Eucerin (the "test mixture") was then applied to the same area of the forearm twice and rubbed in thoroughly each time. A Woods lamp examination for florescence was performed before and after the application of the test mixture. FIG. 3 shows PpIX induced florescence under UV illumination immediately after application of test mixture. The test mixture is strongly absorbing in the UV range, so the area where the test mixture was applied appears as a dark spot. However, there are strong areas of fluorescence in the test mixture application zone. Under visual illumination (no figure) the application site is just barely visible as an area with slight yellow tingeing. This yellow tingeing is likely a result of the fact that ferric chloride solution is yellow. The test mixture was allowed to incubate for 1-2 hours. After this, the entire forearm was exposed to 5 J/cm2 of blue light to induce a photoreaction facilitated by PpIX. The treated area was left uncovered and allowed to be exposed to normal lighting conditions, including bright sunshine.

Figure 4:
FIG. 4. shows the treated area of the test subject of FIG. 1 24 hours after light treatment.
Figure 5:
FIG. 5 shows the treated area of the test subject of FIG. 1 72 hours after exposure to the blue light.

FIG. 4 shows the treated area 24 hours after light treatment. Mild puncate erythema was observed in the ALA treated area to which the test mixture was not applied. Little or no erythema was observed in the area in which the test mixture was applied. The ink locator dots indicating the treated area were applied at the time the test mixture was applied but after the FIG. 3 was taken. Very slight discoloration can still be observed in the test mixture application area, but this is the result of staining and not phototoxicity or some other photo-induced reaction. FIG. 5 shows the test area 72 hours after exposure to the blue light. Mild erythema is still present in the un-treated area, but the treated area shows no signs of erythema. Thus, this example demonstrates a method and composition for preventing the phototoxic side effects of PDT.

While preferred embodiments have been illustrated and described, it should be understood that changes and modifications can be made in accordance with ordinary skill in the art without departing from the invention in its broader aspects as defined herein.

What is claimed is:

1. A method of reducing post-photodynamic treatment photosensitivity in a patient comprising:
   administering to a patient in need thereof a photosensitizing compound selected from the group consisting of precursors of protoporphyrin IX 5-aminolevulinic acid and esters thereof and porphobilinogen,
   subsequently exposing said patient to a therapeutic light source for photodynamic therapy, and
   simultaneously with or subsequently to said exposing, administering to said patient an effective amount of a porphyrin complexing molecule.

2. The method of claim 1, wherein the protoporphyrin IX precursor is 5-aminolevulinic acid.

3. The method of claim 1, further comprising administering an effective amount of at least one compound other than the porphyrin complexing molecule which reduces photosensitivity.

4. The method of claim 3, wherein the at least one composition other than the porphyrin complexing molecule which reduces photosensitivity comprises a sunscreen.

5. The method of claim 4, wherein the sunscreen is selected from the group consisting of aminobenzoic acid, padimate O, oxybenzone, titanium dioxide, avobenzone, octocrylene, octyl salicylate, octyl methoxy einnamate, dioxybenzone, oxybenzone, homosalate, octyl methoxycinnamate, menthyl anthranilate, lisadimate phenylbenzimidazole, sulisobenzone, and trolamine salicylate.

6. The method of claim 3, wherein the at least one compound other than the porphyrin complexing molecule which reduces photosensitivity is administered in a composition comprising the photosensitizing compound.

7. The method of claim 3, wherein the at least one compound other than the porphyrin complexing molecule which reduces photosensitivity is administered in a composition comprising the porphyrin complexing molecule.

8. The method of claim 1, wherein the porphyrin complexing molecule is selected from the group consisting of silver (Ag), aluminum (AI), cadmium (Cd), cobalt (Co), chromium (Cr), copper (Cu), iron (Fe), gadolinium (Gd), indium (In), lutetium (Lu), magnesium (Mg), manganese (Mn), nickel (Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn).

9. The method of claim 1, wherein the porphyrin complexing molecule is administered topically.

10. The method of claim 1, wherein the method reduces the duration of photosensitivity.

11. The method of claim 1, wherein the method reduces the severity of photosensitivity.

12. The method of claim 1, wherein the porphyrin complexing molecule comprises a metal.

13. The method of claim 1, wherein the porphyrin complexing molecule is $FeCl_2$.

14. The method of claim 1, wherein the porphyrin complexing molecule is an iron-donating compound.

15. The method of claim 1, wherein the porphyrin complexing molecule is ferric-8-hydroxyquinoline.

16. The method of claim 1, wherein the porphyrin complexing molecule is ferric chloride.

17. The method of claim 1, wherein the photosensitizing compound is administered topically.

18. The method of claim 1, wherein the porphyrin complexing molecule is administered during said exposing step.

19. The method of claim 1, wherein the porphyrin complexing molecule is administered after said exposing step.

20. The method of claim 1, wherein the patient suffers from a skin lesion that preferentially accumulates a photoactivatable porphyrin.

* * * * *